United States Patent
Xu et al.

(10) Patent No.: US 12,286,488 B2
(45) Date of Patent: Apr. 29, 2025

(54) ANTI-DINITOLMIDE MONOCLONAL ANTIBODIES AND HYBRIDOMA CELL STRAIN THAT SECRETES THEM

(71) Applicant: JIANGNAN UNIVERSITY, Jiangsu (CN)

(72) Inventors: Chuanlai Xu, Jiangsu (CN); Jie Liu, Jiangsu (CN); Hua Kuang, Jiangsu (CN); Liguang Xu, Jiangsu (CN); Maozhong Sun, Jiangsu (CN); Liqiang Liu, Jiangsu (CN); Xiaoling Wu, Jiangsu (CN); Changlong Hao, Jiangsu (CN); Shanshan Song, Jiangsu (CN); Yongming Hu, Jiangsu (CN); Qiankun Zheng, Jiangsu (CN)

(73) Assignee: JIANGNAN UNIVERSITY, Wuxi (CN)

( * ) Notice: Subject to any disclaimer, the term of this patent is extended or adjusted under 35 U.S.C. 154(b) by 850 days.

(21) Appl. No.: 17/368,108

(22) Filed: Jul. 6, 2021

(65) Prior Publication Data

US 2022/0010029 A1    Jan. 13, 2022

(30) Foreign Application Priority Data

Jul. 8, 2020 (CN) .......................... 202010650631.3

(51) Int. Cl.
| | | |
|---|---|---|
| *C12N 15/13* | (2006.01) | |
| *C07K 16/44* | (2006.01) | |
| *G01N 33/53* | (2006.01) | |

(52) U.S. Cl.
CPC ......... *C07K 16/44* (2013.01); *G01N 33/5308* (2013.01); *G01N 2430/10* (2013.01)

(58) Field of Classification Search
None
See application file for complete search history.

(56) References Cited

U.S. PATENT DOCUMENTS

2015/0249678 A1 * 9/2015 Decime .............. H04L 63/1441
726/22

FOREIGN PATENT DOCUMENTS

| CN | 106588857 A | 4/2017 |
| CN | 106589024 A | 4/2017 |

OTHER PUBLICATIONS

Clark (Protein Engineering of Antibody Molecules for Prophylactic and Therapeutic Applications in Man, 1993, pp. 4-5).*
Galvidis, I, G. Lapa, and M. Burkin. "Group determination of 14-membered macrolide antibiotics and azithromycin using antibodies against common epitopes." Analytical Biochemistry 468(2015):75-82.

* cited by examiner

*Primary Examiner* — Christine J Saoud
(74) *Attorney, Agent, or Firm* — HAUPTMAN HAM, LLP

(57) ABSTRACT

Disclosed is a hybridoma cell strain that secretes anti-dinitolmide monoclonal antibodies applicable to the field of food safety immunoassay methods. The hybridoma cell strain DAS3H10 that secretes anti-dinitolmide monoclonal antibodies has been deposited in Comprehensive Microbiology Center of China Microbial Culture Collection Management Committee (CGMCC), addressed in No. 1 Hospital No. 3 Institute of Microbiology of the Chinese Academy of Sciences, North Chenxi Road, Beijing Chaoyang District in Beijing. It is classified as a monoclonal cell strain. The deposit date is Nov. 28, 2019, and the deposit number is MCCC No. 19165. The monoclonal antibody secreted by the hybridoma cell strain DAS3H10 has a good affinity and high sensitivity to dinitolmide. Because of $IC_{50}$ to dinitolmide up to 9.01 ng/mL, the monoclonal antibody could be used to prepare dinitolmide immunoassay kits and colloidal gold test strips, and can further provide a powerful means for detecting dinitolmide in animal-derived foods.

2 Claims, 3 Drawing Sheets

ANTI-DINITOLMIDE MONOCLONAL ANTIBODIES AND HYBRIDOMA CELL STRAIN THAT SECRETES THEM

BACKGROUND OF THE INVENTION

1. Technical Field

The present invention relates to a hybridoma cell strain that secretes anti-dinitolmide monoclonal antibodies and its application, and belongs to the field of food safety immunoassay.

2. Background Art

Dinitolmide (DTM) is a poultry feed additive that is widely used as a nitroamide anticoccidial drug because of its effective treatment and prevention of coccidiosis. Stability, low toxicity, low resistance and low cost are also the reasons for its widespread use in animal feed. However, the use of excessive and long-acting drugs may lead to residues of veterinary drugs in poultry tissue, and lead to harm to people's health. In addition, the overuse also results in the excretion of veterinary drugs ingested by poultry and animals in the form of metabolites or prototype drugs, which is harmful to the environment. As a result, the Ministry of Agriculture of China and the U.S. Food and Drug Administration have established strict regulations on the maximum residual limits of dinitolmide in animal tissues: no more than 2,000 $\mu g \cdot kg^{-1}$ in fat, no more than 6,000 $\mu g \cdot kg^{-1}$ in liver and kidneys, and no more than 3,000 $\mu g \cdot kg^{-1}$ in muscles.

The conventional detection methods of dinitolmide include high performance liquid chromatography in tandem with mass spectrometry (HPLC-MS/MS), ultra performance liquid chromatography (UPLC), ultra performance liquid chromatography tandem mass spectrometry (UPLC-MS/MS), gas chromatography tandem mass spectrometry (GC-MS/MS) and so on. However, there are various drawbacks associated with these methods to different degrees including, for example, being overly time-consuming, utilizing expensive instruments, and requiring a large number of sample pretreatment procedures. Therefore, the drawbacks associated with these various methods render these methods generally unsuitable for conducting on-site detection of high-throughput analysis of dinitrotolamine. Further, it has been reported that the dinitolmide content of a sample has been reportedly measured by surface-enhanced Raman spectroscopy. However, although such nanotechnology methods are typically highly sensitive and reliable, they are also highly dependent on accurate data acquisition, so an analysis system is required, which means that the usefulness of these nanotechnology methods for on-site detection operation is limited. Therefore, there is an interest in further developing a rapid detection method for on-site applications in order to meet the requirements of government supervision as well as self-inspection of enterprises.

The immunoassay is characterized by low cost, high throughput, high sensitivity and low relative requirements for technicians, so it is suitable for rapid on-site screening of large numbers of samples. The purpose of the present invention is to provide a preparation method for monoclonal antibody hybridoma cell lines with high affinity and detection sensitivity to dinitolmide. The present invention lays the foundation for the development and promotion of indirect competition ELISA kits and colloidal gold test strips.

SUMMARY OF THE INVENTION

Based on the technical problems of the background technology, the purpose of the invention is to provide a hybridoma cell strain that secretes anti-dinitolmide monoclonal antibodies and its application. The monoclonal antibody secreted by the cell strain has an affinity and a sensitivity to dinitolmide, which can be used in establishing an enzyme-linked immunosorbent assay (ELISA) for dinitolmide, or to establish a rapid detection method of colloidal gold immunodialysis test strips.

The technical scheme of the present invention is to provide a hybridoma cell strain DAS3H10 that secretes anti-dinitolmide monoclonal antibodies, which has been deposited in Comprehensive Microbiology Center of China Microbial Culture Collection Management Committee (CGMCC), addressed in No. 1 Hospital No. 3 Institute of Microbiology of the Chinese Academy of Sciences, North Chenxi Road, Beijing Chaoyang District in Beijing. It is classified as a monoclonal cell strain. The deposit date is Nov. 28, 2019, and its deposit number CGMCC No. 19165.

The anti-dinitramine monoclonal antibody is secreted by the hybridoma cell strain DAS3H10 with the deposit number CGMCC No. 19165.

The steps of producing complete immunogen of dinitolmide are as follows: 4.5 mg of 3,5-dinitro-2-methylbenzoic acid, as well as 5.0 mg EDC and 3.7 mg NHS are dissolved in DMF with stirring and activating at room temperature for 6 h to obtain the activating solution. Another 15 mg BSA was dissolved in 3 mL, 0.05M, pH 9.6 carbonate buffer solution. The activating solution was added dropwise to the BSA solution, stirred at room temperature overnight, and then the immunogen was taken out and dialyzed with PBS for 3 days. At last, the immunogen was aliquoted for storage at $-20°$ C., for preserving the immunogen of dinitolmide.

The anti-dinitolmide monoclonal antibodies can then be used for detecting residual dinitolmide in food.

The basic steps for the preparation of the DAS3H10 cell line provided by the invention are:

(1) Preparation and identification of immunogen: 3,5-dinitro-2-methylbenzoic acid, which is a structure analogue of dinitolmide, was used as a raw material and connected to the amino group of the protein carrier with the activated ester method. After the reaction was completed, the complete immunogen and the unconnected small molecule hapten were separated by dialysis. And the complete immunogen was identified by UV-VIS absorption spectrometry.

(2) Immunization of mice: BALB/c mice aged 6-8 weeks were selected for immunization. The immunogen, which was emulsified with Fuchs adjuvant, was injected to the BALB/c mice by subcutaneous injection at multiple points. The Faust complete adjuvant was used for the first immunization, the Faust incomplete adjuvant was used for the booster immunization, and the commixture of the immunogen and normal saline was used for the sprint immunization by intraperitoneal injection. Each immunization dose was half of the previous immunization dose, and the interval between each immunization was three weeks. After the third immunization, blood collection was collected every one week for the detection of serum titer and inhibition.

(3) Cell fusion and cell line establishment: the cell fusion of mouse spleen cells and mouse myeloma cells was accomplished by polyethylene glycol (PEG 2000). After cultured culturing in HAT medium, there was detection of positive cells wells by indirect ELISA, and further detection of the inhibition effect of positive cell wells by indirect competition ELISA. Positive cell wells with the best inhibition effect were subcloned three times by limiting dilution assay, and finally the hybridoma cell strain DAS3H10 was finally screened.

(4) Identification of the properties of hybridoma cell strains: the identification of hybridoma cell strains were determined by HRP, and $IC_{50}$, cross-reaction rates and affinity were determined by ELISA.

The Invention has the Advantages of

The beneficial effect of the present invention: (1) The anti-dinitolmide monoclonal antibody obtained by the present invention provides improved dinitolmide detection sensitivity and affinity, and (2) provides a new method of synthesizing dinitolmide immunogen using simplified and effective synthesis steps when compared with available prior art methods.

Biological Preservation Instructions

The hybridoma cell strain that secretes anti-dinitolmide monoclonal antibodies, DAS3H10, has been deposited in Microbiology Center of China Microbial Culture Collection Management Committee CGMCC in Beijing, China, on Nov. 28, 2019, addressed in No. 1 Hospital No. 3 Institute of Microbiology of the Chinese Academy of Sciences, North Chenxi Road, Chaoyang District in Beijing. It is classified as a monoclonal cell strain. And its deposit number MCCC No. 19165.

DESCRIPTION OF PREFERRED EMBODIMENTS

The detailed implementation of the invention is further described as follows. The following embodiments are used to illustrate the invention, but not to limit the scope of the invention. Except for special instructions, the experimental methods used in the following embodiments are all conventional methods. Except as detailed in special instructions, the materials and reagents, etc. referenced and/or used in the disclosure can be obtained from commercial sources.

By using the methods outlined in the present disclosure, those skilled in the art can obtain a monoclonal antibody hybridoma cell strain with a degree of affinity and sensitivity to dinitolmide sufficient for use in detecting dinitolmide. As detailed above, the method involves immunizing mice with a complete immunogen of dinitolmide, cell fusion, growth in HAT medium, and screening of the hybridoma cell culture supernatant by indirect ELISA and indirect competition ELISA.

Implementation 1: As detailed above, the preparation of DAS3H10, a monoclonal antibody hybridoma cell strain comprises:

1. the synthesis of complete immunogens: 3,5-dinitro-2-methylbenzoic acid, which is a structural analog of dinitolmide, was used as a raw material and connected to the amino group of the protein carrier using an activated ester method. After the reaction was completed, the complete immunogen and the unconnected small molecule hapten were separated by dialysis with the complete immunogen then being identified using ultraviolet absorption scanning.

Figure 1B:
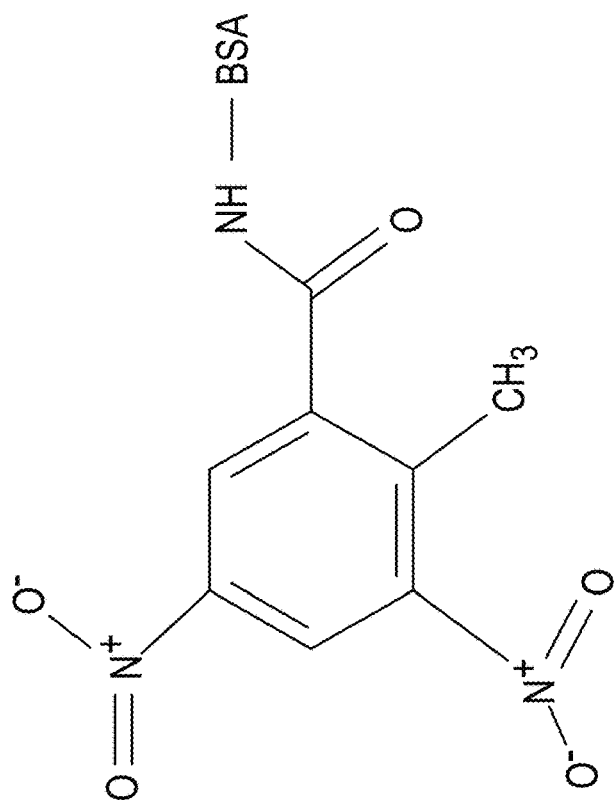
FIGS. 1A and 1B are the chemical structure of hapten (FIG. 1A) and complete immunogens (FIG. 1B).
Figure 1A:
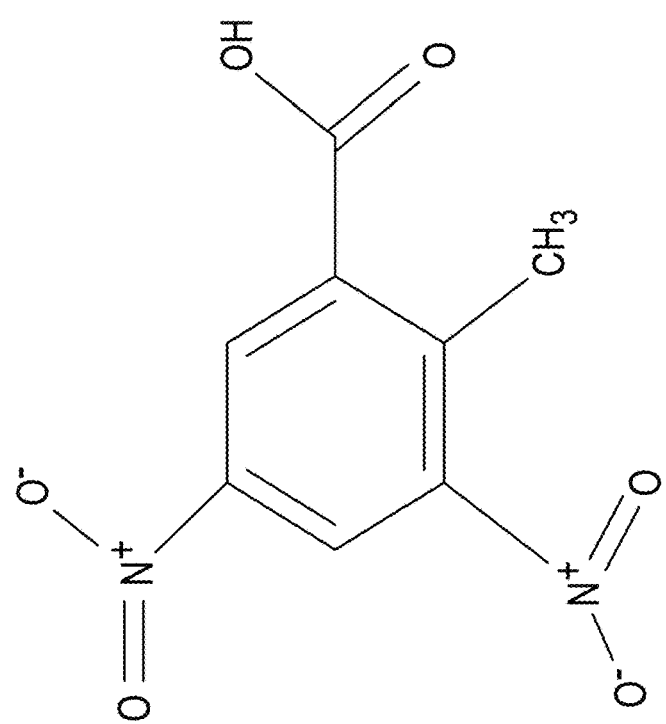
Figure 2:
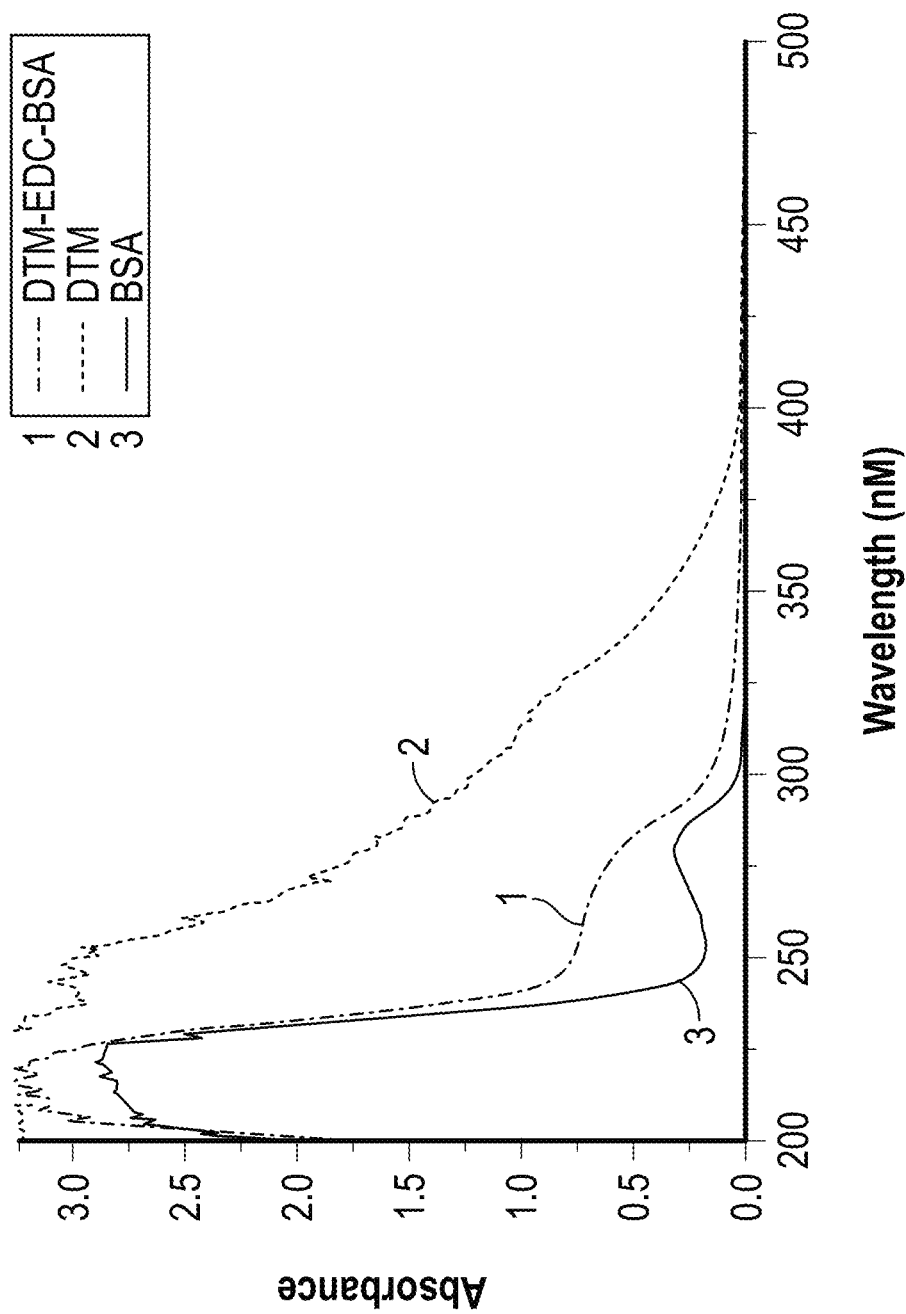
FIG. 2 is the UV absorption spectrum characterization of the immunogens.

The structure of the hapten is shown in FIG. 1A, the structure of the complete immunogen is shown in FIG. 1B, and the UV absorption spectroscopic characterization is shown in FIG. 2.

4.5 mg of 3,5-dinitro-2-methylbenzoic acid, 5.0 mg EDC (1-(3-dimethylamphetamine)-3-ethyl carbon diamide hydrochloride) and 3.7 mg NHS(N-hydroxyamide) were dissolved in DMF (N, N-dimethyl methamphetamine) with stirring and activating at room temperature for 6 h to obtain the activating solution. Another 15 mg BSA (bovine serum protein) was dissolved in 3 mL, 0.05M, pH 9.6 CB (carbonate buffer solution). The activating solution was added dropwise to the BSA solution, stirred at room temperature overnight, and then the immunogen was extracted and dialyzed with PBS for 3 days. At last, the immunogen was aliquoted for storage at −20° C. to preserve the immunogen of dinitolmide.

2. Immunization of mice: BALB/c mice aged 6-8 weeks were selected for immunization. The immunogen (1 mg/mL), which was emulsified with Fuchs adjuvant, was injected to the BALB/c mice by subcutaneous injection at multiple points, with 100 μL for every mice. The Faust complete adjuvant was used for the first immunization, the Faust incomplete adjuvant was used for the booster immunization, and the commixture of the immunogen and normal saline was used for the sprint immunization by intraperitoneal injection. Each immunization dose was half of the previous immunization dose, and the interval between each immunization was three weeks. After the third immunization, blood collection was collected every one week for the detection of serum titer and inhibition. The mice with the best inhibition effect were selected for sprint immunity 18 days after the fifth immunization and were ready for fusion.

3. Cell fusion: Three days after the sprint immunity, the cell fusion was accomplished in accordance with the conventional PEG ASSAYs (polyethyl glycol, molecular weight of 2000), the specific steps are as follows:

(1) The spleen of mice was obtained in aseptic conditions, grinded and then screened through cell strainers with the screen mesh number of 200 mesh, to get the spleen cell suspension which was used for cell counting;

(2) SP2/0 cells were collected and suspended in RPMI-1640 basic medium for cell counting;

(3) Spleen cells and SP2/0 cells were mixed in accordance with the count ratio of 2~10:1. After centrifugation, the cell fusion was carried on with PEG for 1 min. RPMI-1640 basic medium was added from slow to fast. The mixture was centrifuged and the centrifugal suspension was distributed in the RPMI-1640 screening medium containing 20% fetal bovine serum and 2% 50×HAT which was then added to a 96-well cell culture plate and cultured in an incubator with 5% $CO_2$ at 37° C.

4. Cell screening and cell line establishment: during the cell fusion, half of the RPMI-1640 screening medium of the fusion cell was changed on the 3rd day, and all was replaced by the RPMI-1640 screening medium with 20% fetal bovine serum, 1% of 100×HT on the fifth day. The cell supernatant was used for screening on the 7th day, which is divided into two steps: the first step is to screen out the positive cell wells with indirect ELISA, the second step is to detect the inhibition effect of positive cell wells by indirect competition ELISA with dinitolmide used as the standard substance. The cell wells with good inhibition effect of dinitrotolamine were selected to be subcloned with finite dilution assay, and the inhibition effect was detected in the same way. This process was repeated three times to obtain the cell line.

5. Preparation and identification of monoclonal antibody: 1 mL paraffin oil is injected into the enterocoelia of every BALB/c mice aged 8-10 weeks, and the hybridoma cell was injected into the enterocoelia 7 days after the paraffin oil injection. Hydroperitoneum was then collected and purified with caprylic acid-saturated ammonium sulfate to obtain McAb (monoclonal antibody), which was stored at −20° C.

The McAb obtained from the purified hydroperitoneum was identified by McAb subtype identification kit as IgG2a, as shown in Table 1.

TABLE 1

Subtype identification of dinitolmide monoclonal antibodies

| Subtype identification | OD |
|---|---|
| IgA | 0.104 |
| IgG1 | 0.303 |
| IgG2a | 2.233 |
| IgG2b | 0.221 |
| IgG3 | 0.112 |
| IgM | 0.023 |

The $IC_{50}$ of the monoclonal antibodies against dinitolmide was determined to be 9.01 ng/mL in the way of indirect competitive ELISA, which also verified the $IC_{50}$ and the cross-reaction rates of the monoclonal antibodies against dikjuli and so on, as shown in Table 2.

TABLE 2

$IC_{50}$ and cross-reaction rates of dinitolmide monoclonal antibodies to dinitolmide, dikjuli, torquoly, nicarbazine

| | $IC_{50}$ (ng/mL) | cross-reaction rates |
|---|---|---|
| dinitolmide | 9.01 | 100% |
| dikjuli | >500 | <5% |
| torquoly | >500 | <5% |
| nicarbazine | >500 | <5% |

6. Antibody application: The McAb obtained from the purified hydroperitoneum of DAS3H10 hybridoma cell strain was used in additive reclamation test of dinitolmide ELISA. The specific steps are as follows:

(1) 96-ELISA plate was coated by ENR-OVA composed of 0.1 g/mL dinitolmide diluted with carbonate buffer (CBS) with 100 μL per well at 37° C. for 2 h. The plate was then washed with 200 μL PBST per well each time for 3 min for three times and then dried.

(2) The plate was sealed with 0.2% gelatin CBS, 200 μL per well at 37° C. for 2 h. The plate was washed with 200 μL PBST per well each time for 3 min for three times and dried then.

Figure 3:
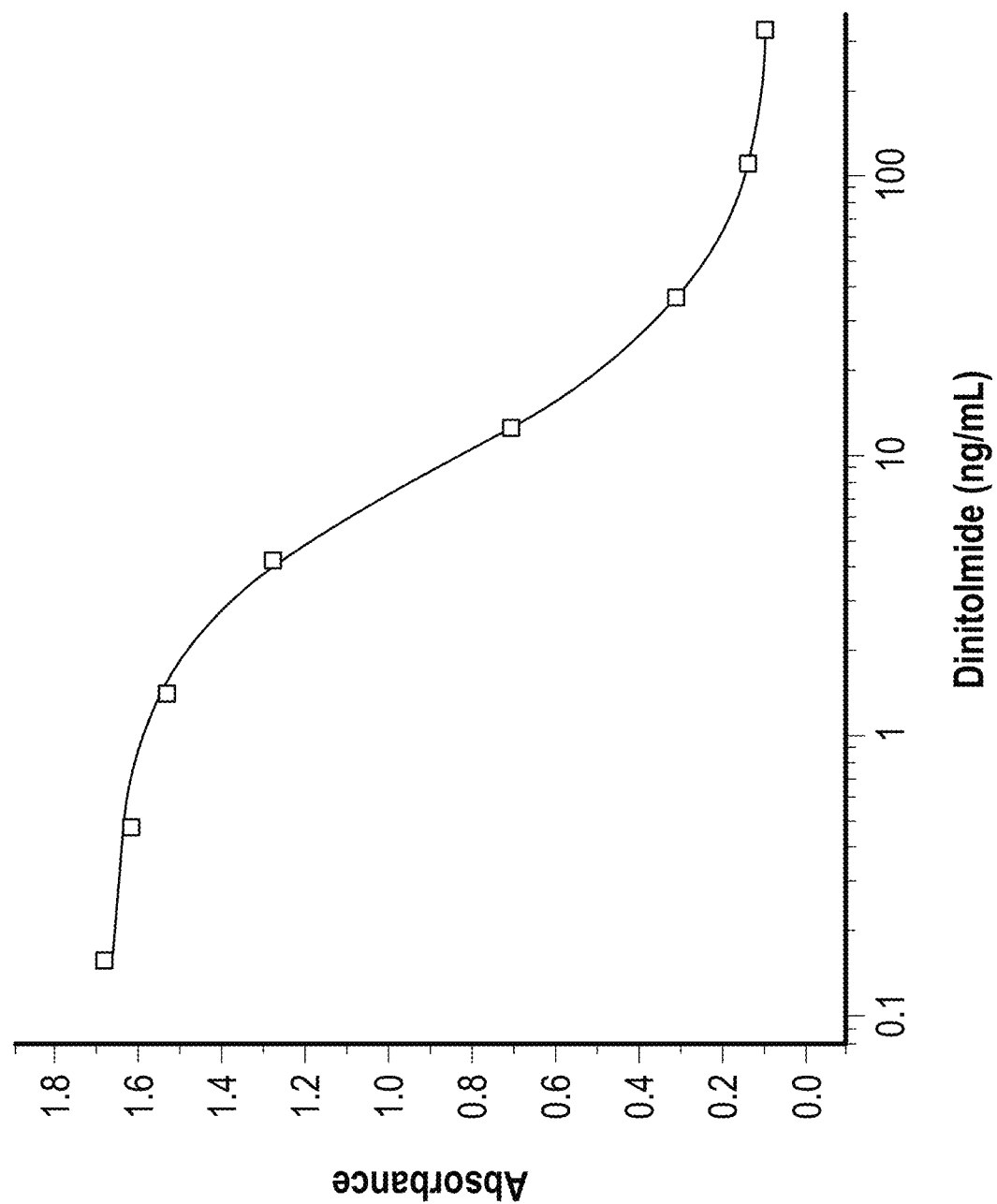
FIG. 3 is the standard inhibition curve of dinitolmide monoclonal antibody.

(3) A standard solution of dinitolmide with phosphate buffer (PBS) was configured with 0, 0.02, 0.05, 0.1, 0.2, 0.5, 1.0, 2.0 μg/L, respectively. The standard solution and the sample extract were respectively added to the closed ELISA plate, 50 μL per well. Each sample was added to 3 wells. And then 50 μL anti-dinitolmide monoclonal antibody diluted by 1:16000 was added. After the reaction for 0.5 h at 37° C., the ELISA plate was then washed and dried;

(4) 100 μL sheep anti-rat IgG abcam which is diluted with PBS with 0.1% gelatin by 1:3000 and marked with HRP was added each well for 0.5 h at 37° C., the Plate was then washed and dried;

(5) 100 μL TMB (color solution) was added to every well for color rendering for 15 min at 37° C., and then 50 μL 2M $H_2SO_4$ was added as termination fluid, and the UV absorption was detected and plotted. The standard inhibition curve of the dinitolmide monoclonal antibody is shown in FIG. 3.

(6) Adding recovery and sample pre-treatment: three different doses of dinitolmide standard substance, 50 ng, 100 ng, 200 ng, was respectively added into 5 g fresh or refrigerated milk. The mixture was placed in a 50 mL centrifuge tube with 1 mL 50% potassium hydroxide solution dropped in slowly. Keep on oscillating fully on the vortex mixer for 10 min, with 20 mL ethyl acetate dropped in slowly. After the centrifuge at 3000 r/min for 5 min, 4 mL of supernate was transferred to another centrifuge tube, which was then blown by dry nitrogen and added in 1 mL PBS with 10% methanol. A 50 μL sample was then extracted and transferred for testing. The recovery rates were 91.2%, 101.5% and 95.6%, respectively, resulting from adding recovery tests with indirect competition ELISA.

Configuration of the Solution:

Carbonate buffer (CBS): $Na_2CO_3$ 1.59 g and $NaHCO_3$ 2.93 g respectively dissolved in a small amount of ultrapure water and mixed, and then added to about 800 mL with ultrapure water. The pH was adjusted to 9.6. The CBS was adjusted to 1000 mL by adding ultrapure water and stored at 4° C. for later use;

Phosphate buffer (PBS): 8.00 g NaCl, 0.2 g KCl, 0.24 g $KH_2PO_4$, 3.62 g $Na_2HPO_4$ 12 $H_2O$ were dissolved in 800 mL pure water with pH adjusted to 7.2 to 7.4 by NaOH or HCl, and adjusted to a total volume of 1000 mL;

PBST: PBS with 0.05% Tween 20;

TMB: A liquid: $Na_2HPO_4$ 12$H_2O$ 18.43 g, citric acid 9.33 g, dissolved in pure water and adjusted to a total volume of 1000 mL; B liquid: 60 mg TMB dissolved in 100 mL ethylene glycol. TMB is the mixture of A and B liquids with a volume ratio of 1:5. The A and B liquids could be mixed just when needed.

While embodiments of the present invention have been illustrated and described, various modifications and improvements can be made by persons skilled in the art. It is intended that the present invention is not limited to the particular forms as illustrated, and that all the modifications not departing from the spirit and scope of the present invention are within the scope as defined in the appended claims.

What is claimed is:

1. A hybridoma cell strain that secretes anti-dinitolmide monoclonal antibodies comprising a hybridoma cell strain named DAS3H10 has been deposited in Comprehensive Microbiology Center of China Microbial Culture Collection Management Committee (CGMCC) on Nov. 28, 2019, assigned the deposit number CGMCC No. 19165, which is maintained at No. 1 Hospital No. 3 Institute of Microbiology of the Chinese Academy of Sciences, North Chenxi Road, Chaoyang District in Beijing, and classified as a Monoclonal Cell Line.

2. The anti-dinitolmide monoclonal antibodies that are secreted by the hybridoma cell strain of claim 1, the hybridoma cell strain named DAS3H10 and assigned the deposit number CGMCC No. 19165.

* * * * *